United States Patent [19]

DeFusco et al.

[11] Patent Number: 4,675,414
[45] Date of Patent: Jun. 23, 1987

[54] MALEIMIDOMETHYL-CARBONATE POLYETHERS

[75] Inventors: Albert A. DeFusco; Eugene C. Martin, both of Ridgecrest, Calif.

[73] Assignee: The United States of America as represented by the Secretary of the Navy, Washington, D.C.

[21] Appl. No.: 710,249

[22] Filed: Mar. 8, 1985

[51] Int. Cl.$^4$ ............... C07D 405/12; C07D 207/452; C08L 69/00
[52] U.S. Cl. .................................. 548/521; 548/548; 526/262
[58] Field of Search ................ 526/262; 548/548, 521

[56] References Cited

U.S. PATENT DOCUMENTS

| | | | |
|---|---|---|---|
| 2,743,260 | 4/1956 | Tawney | 548/548 |
| 2,790,787 | 4/1957 | Tawney | 526/262 |
| 3,729,446 | 4/1973 | Holub et al. | 526/262 |
| 3,855,180 | 12/1974 | Schroefer | 526/262 |
| 4,288,583 | 9/1981 | Zahir et al. | 526/262 |
| 4,548,990 | 10/1985 | Mueller et al. | 526/262 X |

*Primary Examiner*—Richard L. Raymond
*Assistant Examiner*—W. B. Springer
*Attorney, Agent, or Firm*—W. C. Townsend; W. Thom Skeer

[57] ABSTRACT

Aliphatic polyethers having at least two N-methylmaleimide groups chemically joined thereto by a carbonate linkage are provided and a method for making such compounds. The hydroxy-terminated aliphatic polyether, such as polypropylene glycol, is initially reacted with carbonyl chloride to form the chloroformate. The polyether chloroformate derivative is then reacted with N-hydroxymethylmaleimide yielding the bis or tris(maleimidomethyl)carbonate of said polyether.

8 Claims, No Drawings

MALEIMIDOMETHYL-CARBONATE POLYETHERS

BACKGROUND OF THE INVENTION

1. Field of the Invention

This invention relates to aliphatic hydroxy-terminated polyether compositions. More specifically it relates to aliphatic hydroxy-terminated polyether compositions having at least two chemically combined N-methylmaleimide groups joined directly to said polyether by a carbonate linkage.

2. Description of the Prior Art

Maleimide terminated polymers and their synthesis are known. The synthesis of maleimide terminated polymers usually involves the reaction of amine terminated polymers and maleic anhydride in two steps. The later cyclodehydration reaction step often results in low to moderate yields. This is due primarily to elevated reaction temperatures which may result in thermal polymerization of the maleimide group or formation of acetamide derivatives. Holub et al., in U.S. Pat. No. 3,729,446 describe imido-substituted polyester compositions wherein the aromatic polyester and the imido radical are joined via a divalent organo connective. However the prior art is noninstructive in the synthesis of imido-substituted aliphatic polyether compositions.

SUMMARY OF THE INVENTION

According to the present invention maleimide terminated aliphatic polyethers are synthesized under mild conditions and in two efficient steps from corresponding hydroxy-terminated aliphatic polyethers. The polyethers can be produced by effecting reaction between a hydroxy-terminated aliphatic polyether and phosgene (carbonyl chloride) to form the intermediate chloroformate. The chloroformate is then reacted with N-hydroxymethylmaleimide yielding an aliphatic methylmaleimide-terminated polyether having at least two chemically combined N-methylmaleimide groups of the formula:

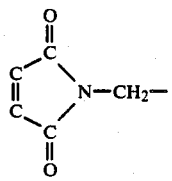

joined directly to the polyethe by a carbonate linkage of the formula:

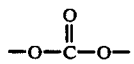

Among the polyethers which may be used according to the present invention are polyoxyalkyl derivatives of glycols such as 1,4-butanediol, 1,4-cyclohexanedinol, propylene glycol, ethylene glycol, diethylene glycol, triethylene glycol, polytetrahydrofurans etc., 1,3-butylene glycol, 1,4-butylene glycol, isomers of acetates of dihydroxybenzene, bisphenols, such as diphenylolpropane, and halogenated bisphenols.

The polyoxyalkyl derivatives of triols, including glycerine, 1,2,6-hexanetriol, trimethylolpropane, and pentaerythritol may also be employed.

OBJECTS OF THE INVENTION

An object of this invention is the synthesis of imido-substituted polyether compositions.

Another object of this invention is an efficient two-step synthesis of imido-substituted polyethers from an aliphatic hydroxy-terminated polyether.

Yet another object of this invention is the synthesis of imido-substituted polyether compositions having at least two N-methylmaleimide groups chemically joined directly to the polyether by a carbonate linkage.

These and other objects of the invention will become apparent from the following examples.

DESCRIPTION OF THE PREFERRED EMBODIMENT

The preferred embodiment may be understood from the following specific examples given by way of illustration and not by way of limitation.

EXAMPLE 1

The synthesis of the bis(maleimidomethyl)carbonate of polypropylene glycol (M.W. 425) was as follows. In a suitable container equipped with a stirrer, excess phosgene was bubbled into 10 ml of dry dimethoxyethane at $-3°$ C. under $N_2$. Dry pyridine (7.6 ml., 0.0941 moles) was then added slowly via syringe through a rubber septum to provide a suspension of the pyridine/phosgene salt. A solution of 20 (0.0471 moles) of polypropylene glycol (m.w. 425) in 35 ml. of dry dimethoxyethane was added dropwise at $-3°$ C. over a period of 45 minutes The reaction mixture was then allowed to stir overnight at room temperature under $N_2$. Ether (50 ml.) was then added and the resulting white precipitate removed by filtration and rinsed with an additional 50 ml. of ether. The filtrate was evaporated to afford 25.2 grams (97%) of the bischloroformate of the polypropylene glycol of molecular weight 425 as identified by IR and proton NMR spectroscopy.

The bischloroformate (5 grams, 0.0091 moles) was then dissolved in 20 ml. of dry dimethoxyethane and the reaction flask was purged with $N_2$. A solution of 2.3 grams (0.0182 moles) of N-hydroxymethylmaleimide in 30 ml. of dry dimethoxyethane containing 1.5 ml. (0.0182 moles) of dry pyridine was added dropwise at ambient temperature. The reaction mixture was allowed to stir overnight under $N_2$. Ether (75 ml.) was added and the resulting white precipitate was removed by filtration and washed with an additional 25 ml. of ether. The filtrate was evaporated to yield a light pink oil which was taken up in 50 ml of fresh ether and then passed over a 3 cm. diameter by 9 cm long column of silica gel. Once the polymer begins to elute from the column, 150 ml. of eluant was collected and evaporated to yield 5.2 grams (80%) of the bis(maleimidomethyl) carbonate of the polypropylene glycol. Equivalent weight analysis by proton NMR gave 249 g/mole for the product.

EXAMPLE 2

The synthesis of the tris(maleimidomethyl)carbonate of the polypropyleneoxy derivative of trimethylol propane having a molecular weight of 4542, was prepared according to the procedure of Example 1 except that silica gel chromatography was performed with acetone as the solvent. The product was isolated in 87% yield and was identified by IR and proton NMR spectroscopy. Equivalent weight analysis by proton NMR gives 1,779 g/mole.

Obviously many modifications and variations of the present invention are possible in light of the above teachings. It is therefore to be understood that within the scope of the appended claims the invention may be practiced otherwise than as specifically described.

We claim:

1. A method for the preparation of maleimidomethyl carbonate terminated polyalkylene oxides of the formula:

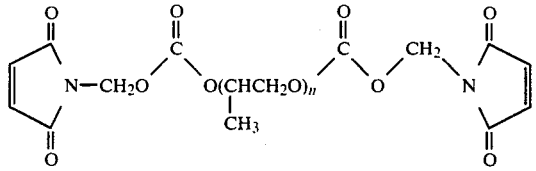

where n is from 6 to 7, said method comprising:
adding a solution of carbonyl chloride at −3° C. to a solution of a polyalkylene oxide at −3° C.;
stirring said reaction mixture for about 12 hours at room temperature under an inert gas;
adding ether to said reaction mixture to form a precipitate and filtering said precipitate;
dissolving said precipitate in dry dimethoxyethane at room temperature under an inert gas;
adding a solution of N-hydroxymethylmaleimide at room temperature under an inert gas;
stirring said reaction mixture for about 12 hours under an inert gas;
adding ether to said reaction mixture to cause a precipitate and filtering said precipitate; and
evaporating said filtrate to yield the product.

2. A method according to claim 13 wherein said polyalkylene oide is a polypropylene glycol having ether linkages and a molecular weight of about 425.

3. As a composition of matter the bis(-maleimidomethyl) carbonate of polypropylene glycol of molecular weight 425.

4. A method for the preparation of maleimidomethyl carbonate terminated polyalkylene oxides of the formula:

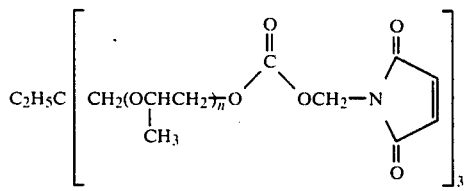

where n is from 23 to 24, said method comprising:
adding a solution of carbonyl chloride at −3° C. to a solution of a polyalkylene oxide at −3° C.;
stirring said reaction mixture for about 12 hours at room temperature under an inert gas;
adding ether to said reaction mixture to form a precipitate and filtering said precipitate;
dissolving said precipitate in dry dimethoxyethane at room temperature under an inert gas;
adding a solution of N-hydroxymethylmaleimide at room temperature under an inert gas;
stirring said reaction mixture for about 12 hours under an inert gas;
adding ether to said reaction mixture to cause a precipitate and filtering said precipitate; and
evaporating said filtrate to yield the product.

5. A method according to claim 4 wherein said inert gas is nitrogen gas.

6. A method according to claim 4 wherein said polyalkylene oxide is the polyoxyalkyl derivative of trimethylolpropane with a molecular weight of 4542.

7. A method according to claim 1 wherein said inert gas is nitrogen gas.

8. As a composition of matter the tris(-maleimidomethyl) carbonate of the polypropyleneoxy derivative of trimethylol propane of molecular weight 4542.

* * * * *